US011917366B1

(12) United States Patent
Ali

(10) Patent No.: US 11,917,366 B1
(45) Date of Patent: Feb. 27, 2024

(54) MEMS OPTICAL MICROPHONE

(71) Applicant: AAC ACOUSTIC TECHNOLOGIES (SHENZHEN) CO., LTD., Shenzhen (CN)

(72) Inventor: Taimoor Ali, London (GB)

(73) Assignee: AAC ACOUSTIC TECHNOLOGIES (SHENZHEN) CO., LTD., Shenzhen (CN)

( * ) Notice: Subject to any disclaimer, the term of this patent is extended or adjusted under 35 U.S.C. 154(b) by 0 days.

(21) Appl. No.: 17/952,358

(22) Filed: Sep. 26, 2022

(51) Int. Cl.
| | |
|---|---|
| H04R 23/00 | (2006.01) |
| H04R 1/08 | (2006.01) |
| G01B 11/06 | (2006.01) |
| A61B 5/107 | (2006.01) |
| G01B 11/02 | (2006.01) |

(52) U.S. Cl.
CPC .......... *H04R 23/008* (2013.01); *A61B 5/1076* (2013.01); *G01B 11/026* (2013.01); *G01B 11/0608* (2013.01); *H04R 1/086* (2013.01); *H04R 2201/003* (2013.01); *H04R 2410/00* (2013.01); *H04R 2499/11* (2013.01)

(58) Field of Classification Search
CPC ............ H04R 23/008; H04R 2201/003; H04R 2499/11; H04R 1/086; H04R 2410/00; G01B 11/026; G01B 11/0608; G01B 11/00; A61B 5/1076
See application file for complete search history.

(56) References Cited

U.S. PATENT DOCUMENTS

| | | | | |
|---|---|---|---|---|
| 6,483,619 B1* | 11/2002 | Greywall | ............. | H04R 23/008 398/132 |
| 7,355,720 B1* | 4/2008 | Carr | ..................... | H04R 23/008 356/498 |
| 8,072,609 B1* | 12/2011 | Trivedi | .................... | G01H 9/00 356/486 |
| 2002/0094093 A1* | 7/2002 | Paritsky | ............... | H04R 25/402 381/92 |
| 2005/0241398 A1* | 11/2005 | Suzuki | ..................... | G01H 9/00 73/643 |
| 2011/0058159 A1* | 3/2011 | Weston | ................ | G01B 11/007 356/237.1 |

(Continued)

*Primary Examiner* — Carolyn R Edwards
*Assistant Examiner* — Kuassi A Ganmavo
(74) *Attorney, Agent, or Firm* — W&G Law Group

(57) ABSTRACT

An MEMS optical microphone, including: a shell including an inner cavity and a sound inlet that communicates the inner cavity with outside; an MEMS module including a diaphragm suspended in the inner cavity, when an acoustic pressure is applied, an aperture is formed in the diaphragm, and the size of the aperture increases or decreases with the magnitude of the acoustic pressure applied to the diaphragm; an optoelectronic module including an electromagnetic radiation source and a sensor, the electromagnetic radiation source and the sensor are arranged on opposite sides of the diaphragm, and a light beam emitted by the electromagnetic radiation source passes through the aperture and reaches the sensor; and an integrated circuit module electrically connected with the MEMS module and the optoelectronic module. Advantages of high sensitivity and flat frequency response can be achieved, which provides the potential to further improve the performance of the device.

8 Claims, 1 Drawing Sheet

(56) References Cited

U.S. PATENT DOCUMENTS

| | | | |
|---|---|---|---|
| 2015/0365770 A1* | 12/2015 | Lautenschlager | H04R 19/005 381/172 |
| 2019/0084827 A1* | 3/2019 | Dehe | H04R 19/005 |
| 2022/0167096 A1* | 5/2022 | LaColle | H04R 23/008 |
| 2022/0408198 A1* | 12/2022 | Sagberg | G01B 11/14 |

* cited by examiner

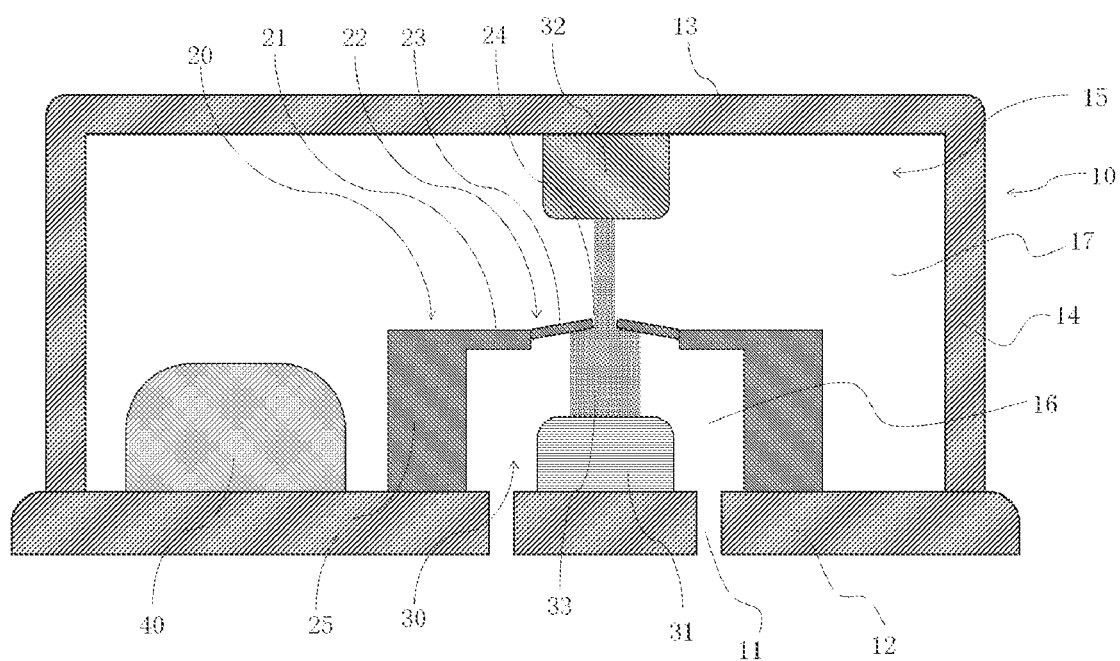

MEMS OPTICAL MICROPHONE

TECHNICAL FIELD

The present disclosure relates to the technical field of microphones and, in particular, to a MEMS optical microphone.

BACKGROUND

Conventional microphones are based on capacitors, where a diaphragm vibrates with sound waves and generates a voltage change upon changing a distance between plates of the capacitors, thereby achieving acoustic-electrical conversion.

Optical microphone is a new type of microphone. An optical microphone generally includes: an optoelectronic module, an application specific integrated circuit (ASIC), and a micro-electro-mechanical system (MEMS). The optoelectronic module can emit light to the MEMS, and receive light reflected by the MEMS. When sound wave actuates the diaphragm of the MEMS, the diaphragm vibrates slightly and thus changes intensity and phase of the light reflected back to the optoelectronic module. The optoelectronic module converts the intensity and phase signal of the reflected light into an electrical signal, and transmits to the ASIC, so as to realize transformation from acoustic signal to optical signal and then to electrical signal.

With the increasingly high experience requirements of consumers, it is necessary to propose an MEMS optical microphone with better performance.

SUMMARY

The purpose of the present disclosure is to provide an MEMS optical microphone to solve the technical problems in the related art.

The present disclosure provides a MEMS optical microphone, including: a shell including an inner cavity and a sound inlet that communicates the inner cavity with outside; an MEMS module including a diaphragm suspended in the inner cavity, wherein when an acoustic pressure is applied to the diaphragm, an aperture is formed on the diaphragm, and a size of the aperture increases or decreases with a magnitude of the acoustic pressure applied to of the diaphragm; an optoelectronic module including an electromagnetic radiation source and a sensor, the electromagnetic radiation source and the sensor are arranged on opposite sides of the diaphragm, and a light beam emitted by the electromagnetic radiation source passes through the aperture and reaches the sensor; and an integrated circuit module electrically connected with the optoelectronic module.

As an improvement, the electromagnetic radiation source includes a laser or a light emitting diode, and the sensor includes a photodiode.

As an improvement, a light flap is arranged in the diaphragm, and a first end of the light flap is connected to a surface wall of the diaphragm, and a second end of the light flap is suspended; when an acoustic pressure is applied, an aperture is formed by the light flap.

As an improvement, the light flap is formed in a hinge region in the diaphragm.

As an improvement, a size of the light beam is larger than a maximum size of the aperture.

As an improvement, the inner cavity includes a first shell wall, a second shell wall, and a side shell wall connecting the first shell wall and the second shell wall, the first shell wall is opposite to the second shell wall, the MEMS module and the integrated circuit module are arranged on the first shell wall, and the sound inlet is arranged on the first shell wall or the second shell wall.

As an improvement, a plurality of sound inlets are provided, and the plurality of sound inlets are distributed on the first shell wall or the second shell wall.

As an improvement, the sound inlet is provided on the first shell wall, the MEMS module further includes a support arm, and opposite ends of the support arm are respectively connected to the diaphragm and the first shell wall, so as to suspend the diaphragm in the inner cavity; the diaphragm divides the inner cavity along an incident direction of sound wave into a front cavity and a rear cavity, and the front cavity covers the sound inlet.

As an improvement, the electromagnetic radiation source is arranged on the first shell wall, the sensor is arranged on the second shell wall, and the electromagnetic radiation source and the sensor are positioned directly facing the aperture.

As an improvement, the diaphragm has a shape symmetrical about a geometric center thereof.

As an improvement, the aperture is provided at the geometric center of the diaphragm.

Compared with the related art, the present disclosure provides an aperture on the diaphragm, the aperture opens and closes in response to a pressure or sound signal applied to the diaphragm, and controls the amount of light transmitted through the aperture. The passing light beam is converted into an electrical signal, which corresponds to the applied pressure level of the acoustic signal, and has the advantages of high sensitivity and flat frequency response, which provides the potential to further improve the performance of the device.

BRIEF DESCRIPTION OF DRAWINGS

FIG. 1 is a schematic structural diagram of an MEMS optical microphone according to an embodiment of the present disclosure.

REFERENCE SIGNS

10—shell, 11—sound inlet, 12—first shell wall, 13—second shell wall, 14—side shell wall, cavity, 16—front cavity, 17—rear cavity;
20—MEMS module, 21—diaphragm, 22—hinge region, 23—light flap, 24—aperture, 25—support arm;
30—optoelectronic module, 31—electromagnetic radiation source, 32—sensor, 33—light beam;
40—integrated circuit module.

DESCRIPTION OF EMBODIMENTS

Embodiments described below with reference to the accompanying drawings are exemplary and are only configured to explain the present disclosure, but not to be construed as limitations to the present disclosure.

As shown in FIG. 1, an embodiment of the present disclosure provides an MEMS optical microphone, including: a shell 10, a MEMS module 20, an optoelectronic module 30 and an integrated circuit module 40.

The shell 10 has an inner cavity 15 and a sound inlet 11 that communicates the inner cavity 15 with the outside. In one embodiment according to the present disclosure, the inner cavity 15 includes a first shell wall 12, a second shell wall 13, and a side shell wall 14 connecting the first shell wall 12 and the second shell wall 13. The first shell wall 12 and the second shell wall 13 are opposite to each other, and the sound inlet 11 is provided on the first shell wall 12 or the second shell wall 13. It should be noted that the side shell wall 14 can be integrally formed with the first shell wall 12 or the second shell wall 13, or formed as an independent part.

The MEMS module 20 includes a diaphragm 21, the diaphragm 21 is suspended in the inner cavity 15, the diaphragm 21 is provided with an aperture 24, and the size of the aperture 24 increases or decreases with the pressure applied to the diaphragm 21. When the optical microphone is in use, sound waves enter into the shell 10 through the sound inlet 11 and actuate the diaphragm 21 and aperture 24. When the diaphragm 21 is actuated, the diaphragm 21 moves upwards (or downwards depending on the type of the microphone) and the diaphragm 21 moves downwards in the opposite direction (or upwards depending on the type of the microphone) just like a standard oscillating structure with specific frequency and displacement. Where the frequency depends on the frequency of the sound wave, and the displacement depends on the pressure of the sound wave. The aperture 24 opens in tandem with the movement of the diaphragm.

In a balanced state when no pressure or sound signal is applied, no sound wave enter into the sound inlet 11, the diaphragm 21 remains in a natural state, and the aperture 24 is closed or slightly open. When the aperture 24 is closed, the light cannot pass through the aperture 24. When the sound wave enters into the sound inlet 11 and actuates the diaphragm 21 and aperture 24 of the MEMS module 20, the amount of light passing through the aperture 24 changes accordingly. When the size of the aperture 24 is larger, the amount of light transmitted is larger, and when the size of the aperture 24 is smaller, the amount of light transmitted is less.

The optoelectronic module 30 includes an electromagnetic radiation source 31 including, for example, an infrared (IR), visible light or ultraviolet (UV) source, which may be a laser or a light emitting diode; and a sensor 32 including a photodiode. The electromagnetic radiation source 31 and the sensor 32 are arranged on opposite sides of the diaphragm 21. In one embodiment, the electromagnetic radiation source 31 is arranged on the first shell wall 12, the sensor 32 is arranged on the second shell wall 13, and the electromagnetic radiation source 31 and the sensor 32 are arranged directly facing the aperture 24. The sensor 32 is configured to receive the light beam 33 emitted by the electromagnetic radiation source 31, and the light beam 33 covers the aperture 24. The vibration of the aperture 24 changes accordingly, and the light amount of the beam 33 also changes synchronously. The light intensity increases with the increase of the sound pressure, and increases with the increase of the size of the aperture 24. When the light beam 33 is received by the sensor 32, the change of the light intensity generates a photocurrent corresponding to the level of the applied sound signal, and the light signal represented by the photocurrent is transmitted to the integrated circuit module 40, to realize the conversion from the acoustic signal to the optical signal and then to the electrical signal.

The integrated circuit module 40 is electrically connected to the optoelectronic module 30 and may be connected to the MEMS module 20. The integrated circuit module (ASIC) 40 includes an electronic circuit that constitutes a control or central processing unit, which drives, controls and perform necessary action to the related electronic and optoelectronic components in the system.

In one embodiment, the aperture 24 is provided on the diaphragm 21, and the aperture 24 is opened and closed in response to the pressure or sound signal applied on the diaphragm 21, and the amount of light transmitted through the aperture 24 is controlled, and thus the light passing through the aperture 24 is controlled. The light beam 33 is converted into an electrical signal, the electrical signal corresponds to the applied pressure level of the sound signal, and thus achieving the advantages of high sensitivity and flat frequency response, thereby further improving performance of the device.

In one embodiment, a hinge region 22 is formed on the diaphragm 21, a light flap 23 is arranged in the hinge region 22. A first end of the light flap 23 is connected to the inner wall surface of the hinge region 22, and a second end of the light flap 23 is suspended. When an acoustic pressure is applied to the diaphragm 21, an aperture 24 is formed in the hinge region 22.

When there is only a single light flap 23 in the hinge region 22, the outer contour surface of the light flap 23 is adapted to the inner contour surface of the hinge region 22. When an acoustic pressure is applied to the diaphragm 21, the aperture 24 is formed between the outer edge of the light flap 23 and the inner wall of the hinge region 22. In a balanced state when no pressure or sound signal is applied, the light flap 23 will block the hinge region 22, and the beam 33 emitted by the electromagnetic radiation source 31 cannot pass through. When the sound wave enters into the sound inlet 11, the diaphragm 21 and the light flap 23 of the MEMS module 20 are actuated, the diaphragm 21 vibrates slightly and the light flap is opened. After the sound wave passes through the aperture 24 and reaches the sensor 32. The greater the magnitude the pressure variation the greater the displacement of the light flap 23, and the larger the amount of the beam 33 will pass through. The sensor 32 receives this beam 33, and the change in light intensity generates a photocurrent corresponding to the level of the applied sound signal.

When a plurality of light flaps 23 are provided in the hinge region 22, the structure formed by the plurality of light flaps 23 is adapted to the inner contour surface of the hinge region 22. When sound pressure is applied, an aperture 24 is formed between outer edges of the plurality of light flaps 23. In a balanced state when no pressure or sound signal is applied, several light flaps 23 will block the hinge region 22, and the beam 33 emitted by the electromagnetic radiation source 31 cannot pass through. When the sound wave enters into the sound inlet 11, several light flaps 23 are opened, and an aperture 24 is formed between the outer edges of the adjacent light flaps 23. The light beam 33 emitted by the electromagnetic radiation source 31 passes through the aperture 24 and reaches the sensor 32. The greater the magnitude of the sound pressure, the greater the angle of the light flap 23 is opened, and the larger the amount of the beam 33 will pass through.

In embodiments of the present disclosure, the size of the light beam 33 is larger than the maximum size of the aperture 24. When the aperture 24 expands to the limit position, the size of the aperture 24 is the largest. At this time, the aperture 24 is still within the coverage of the beam 33. If the size of the beam 33 is smaller than the maximum size of the aperture 24, when the aperture 24 is opened to the maximum size, the amount of the transmitted light beam 33 has already reached the maximum value. In this case, when the size of the aperture 24 is further opened due to the change of the sound signal, such as when the size of the aperture 24 reaches the maximum size, the amount of light passing through the aperture 24 will remain unchanged. As a result, a constant photocurrent is recorded in the sensor 32 for an acoustic signal of this level. This means that even though the aperture 24 can change its size, the sensor 32 will limit the detection of certain levels of sound signals. This will limit the dynamic range of the sensor 32. By setting the size of the light beam 33 emitted by the electromagnetic radiation source 31 to be larger than the maximum size of the aperture 24, the dynamic range of the MEMS optical microphone is improved, and a wider range of sound signals can be sensed, thus achieving higher sensitivity to linear change of the radiation or light intensity caused by the sound signal.

In one embodiment, a plurality of sound inlets 11 are provided, and the plurality of sound inlets 11 are distributed on the first shell wall 12 or the second shell wall 13 in a circular array. These sound inlets 11 can apply uniform pressure to the diaphragm 21, improve the stability of the diaphragm 21, and thus increase the linear range of the optoelectronic module 30.

Referring to FIG. 1, the sound inlet 11 is provided on the first shell wall 12, and the MEMS module 20 further includes a support arm 25. The opposite ends of the support arm 25 are respectively connected to the diaphragm 21 and the first shell wall 12, so as to suspend the diaphragm 21 in the inner cavity 15. The diaphragm 21 separates the inner cavity 15 along the incident direction of the sound wave to form a front cavity 16 and a rear cavity 17. The front cavity 16 covers the sound inlet 11, and the first shell wall 12 includes a PCB substrate. The front cavity 16 refers to the volume between the diaphragm 21 and the sound inlet 11, and the front cavity 16 is a cavity that does not contain any components, so as to improve its performance. The rear cavity 17 refers to the volume between the diaphragm 21 and the inner volume of the shell 10. The diaphragm 21 of the MEMS module 20 is arranged close to the sound inlet 11, so that the volume of the front cavity 16 is small, and the volume of the rear cavity 17 is large, which is beneficial to further improving the performance.

In embodiments according to the present disclosure, the shape of the diaphragm 21 is symmetrical about the center. The shape of the diaphragm 21 is not limited to a circle, but may also be such as a square which is symmetrical about the center. The diaphragm 21 can be made of a single material, and can also be made of multiple materials such as monocrystalline silicon, silicon nitride, silicon oxide, polycrystalline silicon, polyimide, metals, or any combination thereof.

The aperture 24 is located at the geometric center of the diaphragm 21, and the amplitude is the largest at the center of the diaphragm 21. Small acoustic pressure can also cause the size of the aperture 24 to change, thereby affecting the amount of light passing through the beam 33, and thus improving sensing accuracy of the sensor 32.

The structure, features and effects of the present disclosure have been described in detail above according to the embodiments shown in the drawings. The above are only the preferred embodiments of the present disclosure, but the scope of the present disclosure is not limited by the drawings. Changes made to the concept of the present disclosure, or modifications to equivalent embodiments with equivalent changes, shall fall within the protection scope of the present disclosure as long as they do not exceed the spirit covered by the description and drawings.

What is claimed is:

1. A micro-electro-mechanical system (MEMS) optical microphone, comprising:
   a shell including an inner cavity and a sound inlet that communicates the inner cavity with outside;
   an MEMS module including a diaphragm suspended in the inner cavity and having a shape symmetrical about a geometric center thereof, wherein when an acoustic pressure is applied to the diaphragm, an aperture is formed on the diaphragm, and a size of the aperture increases or decreases with a magnitude of the acoustic pressure applied to of the diaphragm;
   an optoelectronic module including an electromagnetic radiation source and a sensor, wherein the electromagnetic radiation source and the sensor are arranged on opposite sides of the diaphragm, and a light beam emitted by the electromagnetic radiation source passes through the aperture and reaches the sensor; and
   an integrated circuit module electrically connected with the optoelectronic module;
   a size of the light beam is larger than a maximum size of the aperture; the aperture is provided at the geometric center of the diaphragm; the electromagnetic radiation source is disposed opposite to the aperture along a vibration direction of the diaphragm.

2. The MEMS optical microphone according to claim 1, wherein the electromagnetic radiation source includes a laser or a light emitting diode, and the sensor includes a photodiode.

3. The MEMS optical microphone according to claim 1, wherein a light flap is arranged in the diaphragm, and a first end of the light flap is connected to a surface wall of the diaphragm, and a second end of the light flap is suspended; when an acoustic pressure is applied, an aperture is formed by the light flap.

4. The MEMS optical microphone according to claim 3, wherein the light flap is formed in a hinge region in the diaphragm.

5. The MEMS optical microphone according to claim 1, wherein the inner cavity includes a first shell wall, a second shell wall, and a side shell wall connecting the first shell wall and the second shell wall, the first shell wall is opposite to the second shell wall, the MEMS module and the integrated circuit module are arranged on the first shell wall, and the sound inlet is arranged on the first shell wall or the second shell wall.

6. The MEMS optical microphone according to claim 5, wherein a plurality of sound inlets are provided, and the plurality of sound inlets are distributed on the first shell wall or the second shell wall.

7. The MEMS optical microphone according to claim 5, wherein the sound inlet is provided on the first shell wall, the MEMS module further includes a support arm, and opposite ends of the support arm are respectively connected to the diaphragm and the first shell wall, so as to suspend the diaphragm in the inner cavity; the diaphragm divides the inner cavity along an incident direction of sound wave into a front cavity and a rear cavity, and the front cavity covers the sound inlet.

8. The MEMS optical microphone according to claim 5, wherein the electromagnetic radiation source is arranged on the first shell wall, the sensor is arranged on the second shell wall, and the electromagnetic radiation source and the sensor are positioned directly facing the aperture.

* * * * *